United States Patent [19]

Foster

[11] Patent Number: 5,376,096
[45] Date of Patent: Dec. 27, 1994

[54] MEDICAL INSTRUMENT FOR DRIVING A SUTURE NEEDLE

[75] Inventor: Thomas L. Foster, Poland, Ind.

[73] Assignee: Vance Products Inc., Spencer, Ind.

[21] Appl. No.: 170,081

[22] Filed: Dec. 17, 1993

[51] Int. Cl.⁵ .............................................. A61B 17/04
[52] U.S. Cl. ..................................... 606/147; 606/148
[58] Field of Search ................................. 606/145–150

[56] References Cited

U.S. PATENT DOCUMENTS

| | | | |
|---|---|---|---|
| 1,539,221 | 5/1925 | Tennant | 606/147 |
| 2,363,334 | 11/1944 | Jones | 606/147 |
| 3,871,379 | 3/1975 | Clarke | 606/148 |
| 3,921,640 | 11/1975 | Freeborn . | |
| 4,109,658 | 8/1978 | Hughes | 128/340 |
| 4,326,531 | 4/1982 | Shimonaka . | |
| 4,345,601 | 8/1982 | Fukuda | 128/339 |
| 4,406,237 | 9/1983 | Eguchi et al. | 112/169 |
| 4,417,532 | 11/1983 | Yasukata | 112/169 |
| 4,424,898 | 1/1984 | Thyen et al. . | |
| 4,440,171 | 4/1984 | Nomoto et al. | 606/145 |
| 4,484,580 | 11/1984 | Nomoto et al. | 606/146 |
| 4,491,135 | 6/1985 | Klein | 606/147 |
| 4,524,771 | 6/1977 | McGregor et al. . | |
| 4,572,185 | 2/1986 | Rich | 606/145 |
| 4,580,567 | 4/1986 | Schweitzer et al. | 606/147 |
| 4,624,252 | 11/1986 | Weiss . | |
| 4,765,334 | 8/1988 | Weiss . | |
| 4,784,139 | 11/1988 | Demos | 128/340 |
| 4,800,880 | 1/1989 | Catalano | 128/340 |
| 4,827,929 | 5/1989 | Hodge . | |
| 5,015,250 | 5/1991 | Foster | 606/147 |
| 5,300,082 | 4/1994 | Sharpe et al. | 606/147 |

FOREIGN PATENT DOCUMENTS 0342402 11/1989 European Pat. Off. .

OTHER PUBLICATIONS

Semm, K., *Pelviscopy-Operative Guidelines*, D-2300 Kiel 1-F.R.G., 1988, pp. 52-53.

Primary Examiner—Stephen C. Pellegrino
Assistant Examiner—Gary Jackson
Attorney, Agent, or Firm—Richard J. Godlewski

[57] ABSTRACT

A needle driver (100) for fixedly positioning a curved suture needle (101) in a channel (114) of an inner rod (109) thereof and in a preferred 90 degree orientation with respect to the longitudinal axis of the inner rod. The needle driver includes an outer tube (102) with a beveled edge (110) positioned transversely at the distal end thereof. The beveled edge includes a substantially straight segment (119) inclined at a preferred angle with respect to the longitudinal axis of the outer tube. The channel of the inner rod includes an undercut surface (116) and an intermediate surface (117) extending longitudinally therefrom. The undercut surface is formed at a preferred angle with respect the longitudinal axis of the inner rod, whereas the intermediate surface is substantially parallel to the axis. The inclined, substantially straight segment of the outer tube beveled edge and the undercut and intermediate surfaces of the inner rod channel cooperate when urged toward each other to fixedly position a curved suture needle in the desired 90 degree orientation. The needle driver also includes a generally U-shaped spring handle (107) attached proximate the proximal ends (122, 134) of the inner rod and outer tube for urging the outer tube beveled edge and inner rod channels toward each other.

20 Claims, 3 Drawing Sheets

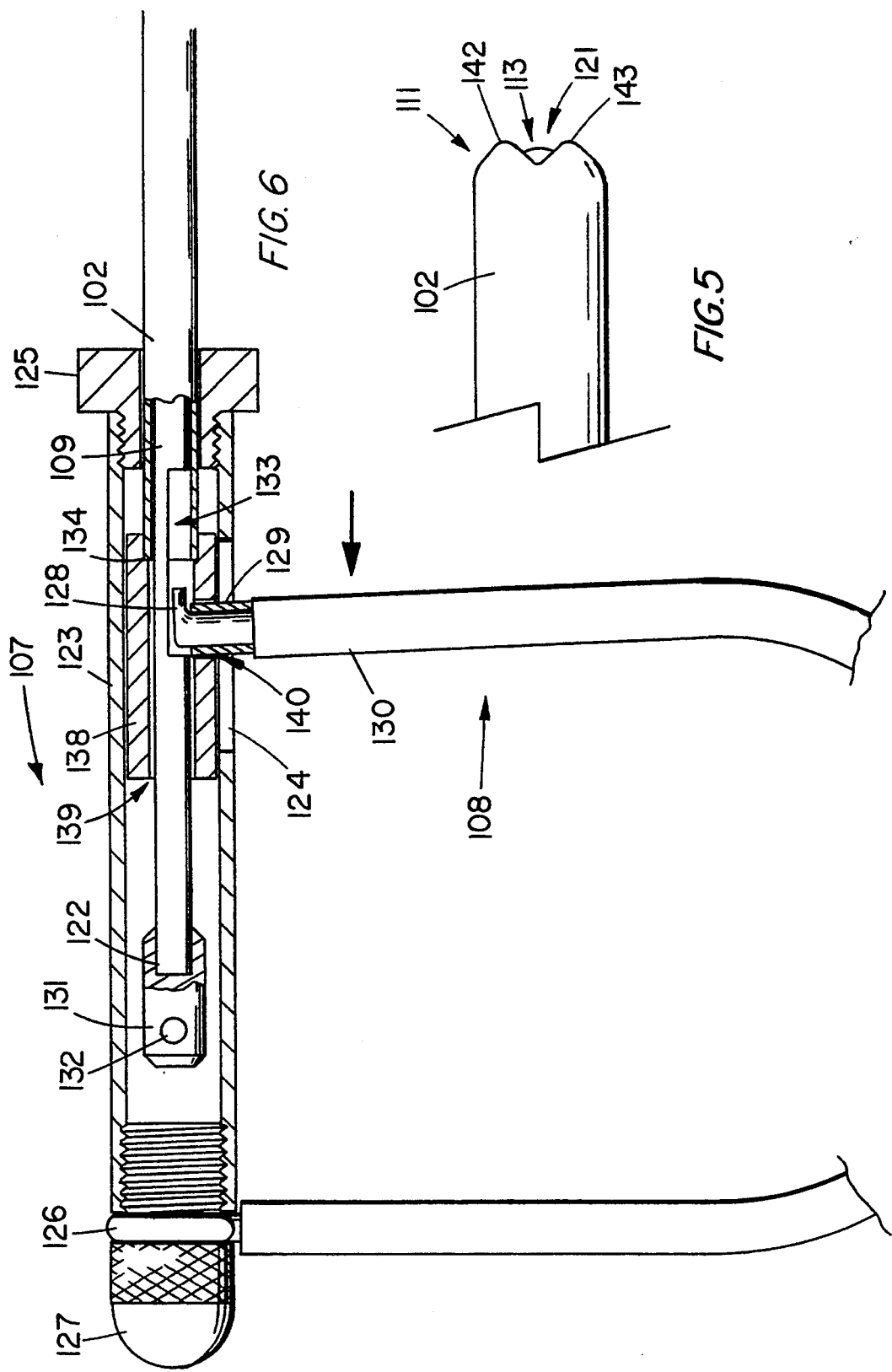

MEDICAL INSTRUMENT FOR DRIVING A SUTURE NEEDLE

TECHNICAL FIELD

This invention relates generally to medical instruments and, in particular, to a medical instrument for driving a suture needle through tissue.

BACKGROUND OF THE INVENTION

A number of manually operated medical and surgical instruments are available for holding or grasping a suture needle. Generally, two varieties of surgical needles are commercially available: straight needles and curved needles. For many situations, straight needles are preferred since they can be more easily handled. In a restricted space, the use of a curved needle is preferred. However, curved needles are very difficult to properly manipulate manually and are invariably utilized in conjunction with needle holders specifically designed for use therewith. The most common needle holders include a configuration somewhat like needle-nose pliers with clamping means for locking the gripping jaws thereof in a fixed position.

A number of curved suture needle holders have been developed for use in invasive type surgery. Such holders commonly have a curved needle affixed to an elongated member for implementing a series of sutures. However, these holders are invariably too bulky to position in restricted surgical site areas and are near impossible to insert through a trocar sheath for endoscopic procedures due to physical size limitations.

With even more confined or limited access endoscopic procedures where the surgical instruments are typically inserted through a trocar sheath, the size of the suture needle is limited as well as the size of the needle holder which must be inserted through the trocar sheath to the surgical site. Endoscopic needle holders typically have a pair of opposing jaws positioned at the distal end of an elongated member which is inserted through the trocar sheath. One jaw is commonly held stationary while the opposing jaw is operated between an open and a closed position. To better grasp the suture needle, the opposing jaws commonly include a plurality of teeth for further grasping the needle.

One problem with these opposing jaw needle holders is the difficulty in maintaining a fixed position when the suture needle is grasped. This problem is further complicated with the use of a curved suture needle which is very common with endoscopic procedures. The curved needle has a tendency to change its position when grasped due to the curvature of the needle. As a result, the surgeon spends considerable time in making just a few sutures with the curved needle.

Another problem is that unless the curved needle is constantly maintained in perfect alignment along its own curvature during suturing, the perforated tissue offers resistance which increases the force necessary to complete the suture. As a result, there is increased tissue trauma with the formation of excessively large openings and possibly even tears in the tissue which may retard proper healing.

Another endoscopic needle driving instrument of the present inventor and disclosed in U.S. Pat. No. 5,015,250 includes an elongated cylindrical tube member with a channel formed near the distal end thereof for receiving a curved suture needle. The channel includes a plurality of surfaces for orienting the needle, and the curved needle is fixedly positioned in the channel by a wedge operable across the channel.

Although useful for its intended purpose, a disadvantage of this endoscopic needle driving instrument is that the suture needle is grasped several millimeters proximal to the distal end of the instrument. As a result, movement of the instrument is restricted in an extremely tight working space. In addition, this needle driving instrument receives a needle in its channel through the top side of the instrument with an upward motion of the distal end of the instrument. As a result, the instrument is positioned underneath the needle for positioning the needle in the channel. Furthermore, the wedge is urged in a forward direction through the channel.

SUMMARY OF THE INVENTION

The foregoing problems are solved and a technical advance is achieved in an illustrative medical instrument such as a needle driver for fixedly positioning therein a curved suture needle in a substantially 90 degree orientation with respect to the longitudinal axis of the instrument and driving the curved suture needle through tissue advantageously during a minimally invasive surgical procedure. The instrument comprises an outer elongated member tube having a beveled edge positioned transversely at a distal end thereof and an inner elongated member rod positioned in the passage of the outer tube. The inner rod has a channel positioned transversely therein proximate the distal end thereof for fixedly positioning a curved suture needle therein advantageously in a preferred orientation with respect to the longitudinal axis thereof. When a curved suture needle is positioned in the channel of the driver, the beveled edge and channel are urged toward each other to fixedly position the curved suture needle in the preferred 90 degree orientation.

The channel of the inner rod advantageously includes a plurality of channel surfaces including an undercut surface and an intermediate surface extending therefrom for fixedly positioning a curved suture needle in the preferred 90 degree orientation. The beveled edge of the outer tube advantageously includes an inclined, substantially straight contact segment for fixedly positioning the curved suture needle in the preferred 90 degree orientation in combination with the undercut and intermediate surfaces of the inner rod channel. The undercut surface of the channel preferably forms an angle of approximately 62 degrees with the longitudinal axis of the inner rod, whereas the intermediate surface is substantially parallel to the axis. However, the angle of the undercut surface can range from approximately 50 degrees to 90 degrees. The inclined, substantially straight contact segment of the beveled edge preferably forms an angle of approximately 12 degrees with respect to the longitudinal axis of the outer tube. The range of the straight contact segment angle is from 8 degrees to 20 degrees. The inclined segment of the outer tube beveled edge in combination with the undercut and intermediate surfaces of the inner rod channel advantageously make contact with the elliptical cross-sectional shape of most commercially available curved needles to fixedly position the needle in the preferred 90 degree orientation. The angles of the undercut and intermediate surfaces of the inner rod channel and the straight segment of the outer tube beveled edge were experimentally found to position a curved suture needle in the preferred 90 degree orientation and to facilitate a large variety of commercially available curved suture needles.

The plurality of surfaces of the inner rod channel also includes a tapered surface extending from the intermediate surface and forming an angle of approximately 13 degrees with respect to the longitudinal axis of the inner rod for advantageously guiding a curved suture needle toward the adjacent intermediate and opposing undercut channel surfaces. Supplementing this tapered channel surface, the beveled edge also advantageously includes a leading, curved contact segment for initially engaging and also guiding the curved suture needle into the undercut and intermediate surfaces of the inner rod channel.

The curved needle driver also includes a handle which is attached proximate the proximal ends of the inner rod and the outer tube and has a spring included therewith for urging the beveled edge of the outer tube and the channel of the inner member toward each other when a curved suture needle is positioned in the inner rod channel. The handle includes a handle tube of which the spring includes a generally U-shaped portion extending laterally from the handle tube for a surgeon to manipulate the driver and, in particular, to operate for engaging and fixedly positioning a curved suture needle in the inner rod channel in the preferred 90 degree orientation.

For advantageously minimizing steps in a minimally invasive surgical procedure, the curved needle driver instrument further comprises a notch extending longitudinally from the distal end of the outer elongated member for pushing a suture knot, which is formed initially external to a patient, through a minimally invasive trocar sheath and to an internal cavity tissue site.

BRIEF DESCRIPTION OF THE DRAWING

FIG. 5 depicts a bottom view of the needle driving medical instrument of FIG. 1 illustrating a notch for use in pushing a knot in suture material; and FIG. 6 depicts a partially sectioned side view of the handle of the needle driver medical instrument of FIG. 1.

DETAILED DESCRIPTION

Figure 1:
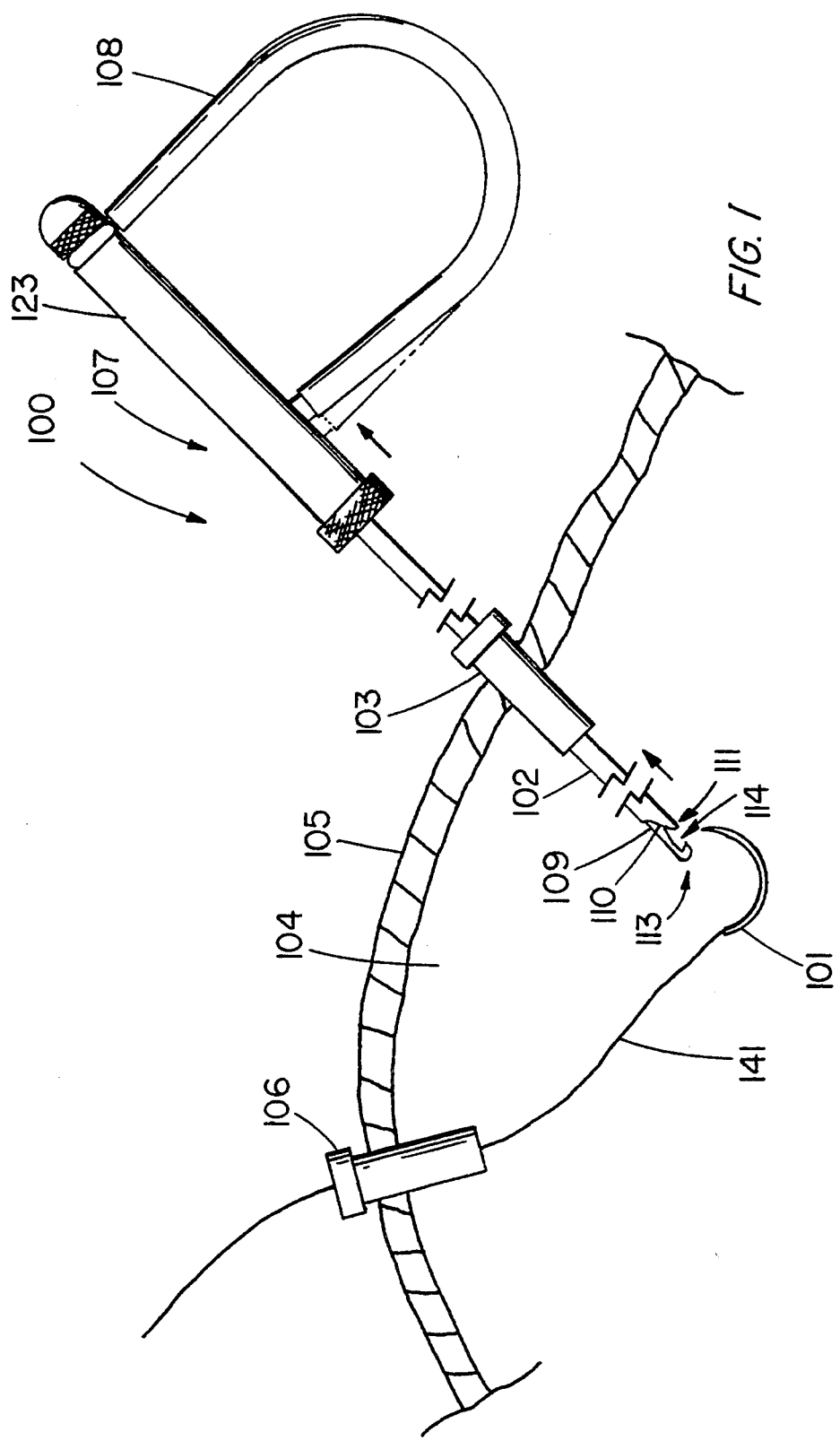
FIG. 1 depicts an illustrative needle driver medical instrument, of the present invention extending through a trocar sheath to an endoscopic surgical site in the peritoneal cavity of a patient.

FIG. 1 depicts medical instrument 100 such as a needle driver for driving a curved suture needle 101 through tissue to form sutures therein. The instrument includes an outer elongated member 102, such as a cylindrical tube, and an inner elongated member 109, such as a cylindrical rod, which are passed through the passage of commercially available trocar sheath 103 and into the peritoneal cavity 104 of a patient 105. The trocar sheath is inserted into the patient for performing a minimally invasive endoscopic surgical procedure. Inner rod 109 includes channel 114 that has a plurality of channel surfaces and is transversely positioned near distal end 113 thereof for receiving and positioning curved suture needle 101 therein. Distal end 111 of the outer elongated member tube includes beveled edge 110 for engaging, urging, and fixedly positioning curved suture needle 101 in a predetermined and, in particular, a perpendicular orientation with respect to the longitudinal axis of the inner rod when seated in the channel of the inner rod.

The curved suture needle is inserted into the peritoneal cavity with the needle driver or alternatively via another trocar sheath 106. Suture thread 141 is connected to one end of the curved needle for suturing tissue together. Needle driver 100 also includes handle 107 at the proximal end thereof and, in particular, attached proximate the proximal ends of outer elongated member tube 102 and inner rod 109. Depicted in a retracted position, the handle includes resilient means such as generally U-shaped spring 108 extending from handle tube 123 retracting outer tube 102 from distal end 113 of inner rod 109. In the released position, spring 108 urges inner rod channel 114 and outer tube beveled edge 110 toward each other for fixedly positioning the curved needle in inner rod channel 114 in a perpendicular orientation. This spring is easily grasped between the thumb and fingers of the surgeon for retracting outer elongated member tube 102 and exposing inner elongated member rod 109 distally from outer tube distal end 111. When distal end 113 of inner elongated member rod 109 and, in particular, channel 114 are extended distally from beveled edge 110 of the outer elongated member tube, the curved suture needle is positioned in the channel and urged between the beveled edge and channel surfaces for fixedly positioning the needle in an approximately perpendicular or 90 degree orientation with respect to the longitudinal axis of the medical instrument.

Figure 2:
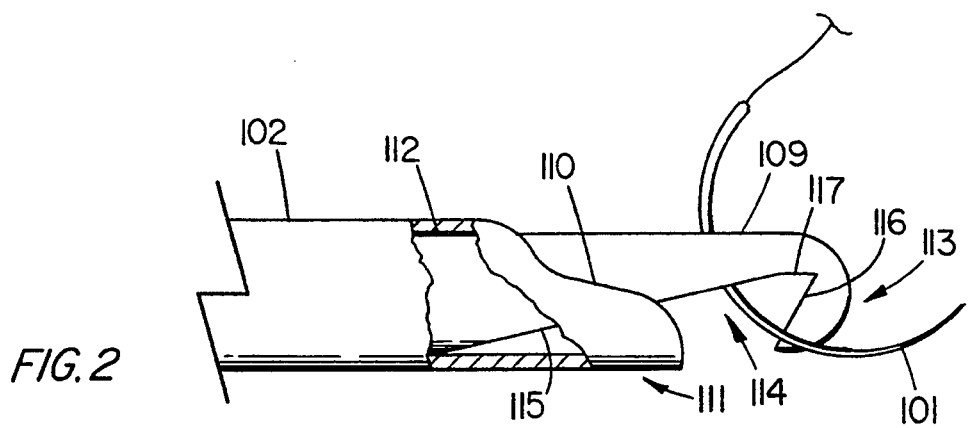
FIG. 2 depicts a partial, sectional side view of the needle driver medical instrument of FIG. 1 with the inner elongated member extended from the outer elongated member for grasping a curved suture needle.

FIG. 2 depicts a partially sectioned side view of distal end 111 of outer elongated member tube 102 of FIG. 1 in a retracted position. The tube includes beveled edge 110 at distal end 111 with passage 112 extending longitudinally therethrough. Inner elongated member rod 109 includes a hemispherically shaped distal end 113 and channel 114 transversely positioned near the distal end for receiving curved suture needle 101 therein. Channel 114 includes a plurality of channel surfaces 115–117 and, in particular, tapered surface 115, undercut surface 116, and intermediate surface 117 extending longitudinally therebetween. Tapered surface forms an angle of approximately 13 degrees with respect to the longitudinal axis of the inner rod, and undercut surface 116 forms an angle of approximately 62 degrees therewith. Intermediate surface 117 is substantially parallel to the axis of the inner rod. The angle of the undercut surface can range from approximately 50 degrees to 90 degrees. Although other needle orientations and surface angles can be achieved, the perpendicular orientation of a curved suture needle in the needle driver was preferred by physicians. When the surgeon positions the medical instrument with a downward motion against a suture needle, tapered surface 115 guides the suture needle toward adjacent intermediate surface 117 and opposing undercut surface 116. The outer tube is extended forward toward the distal end of the inner rod so that beveled edge 110 of the outer tube further guides, urges, and fixedly positions curved suture needle 101 into channel 114.

Figure 3:
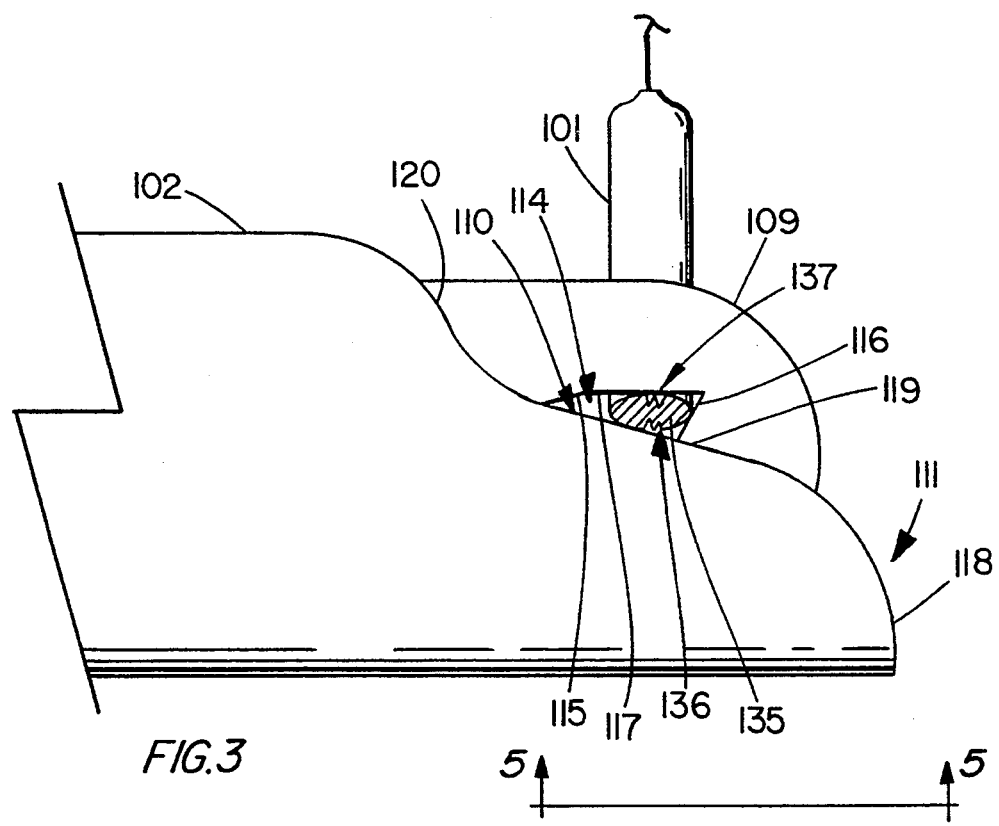
FIG. 3 depicts a partial, sectional side view of the needle driver medical instrument of FIG. 2 with the inner elongated member withdrawn into the passageway of the outer elongated member for fixedly positioning the curved suture needle about the distal end of the instrument.

FIG. 3 depicts a partially sectioned side view of distal end 111 of outer elongated member tube 102 of FIG. 1 in an extended position. The instrument handle (not shown) is released and urging the outer tube forward. Beveled edge 110 engages and fixedly positions curved suture needle 101 in channel 114 of inner rod 109. Beveled edge 110 at distal end 111 of the outer tube includes a plurality of segments 118-120. Leading, curved contact segment 118 initially engages and guides the curved suture needle into channel 114 often with the cooperation of tapered surface 115. Beveled edge 110 also includes intermediate, substantially straight contact segment 119 and trailing, contact segment 120. As the distal end of the outer tube is urged forward, straight contact segment 119 seats against and fixedly positions curved suture needle 101 in channel 114 against cooperating undercut and intermediate channel surfaces 116 and 117. Straight contact segment 119 inclines at an angle of approximately 12 degrees with respect to the longitudinal axis of the outer tube. However, suitable results are obtainable when the angle ranges from 8 degrees to 20 degrees. The straight contact segment and undercut and intermediate surfaces cooperate to fixedly position the needle in the channel at a perpendicular orientation with respect to the longitudinal axis of the outer tube or inner rod. As a result, the curved needle makes contact with the driver at five points: three on the channel and two on the beveled edge. The contact points fix the orientation of a curved needle with respect to the longitudinal axis of the inner rod.

Suture needle 101 at a point approximately midway through its curvature exhibits an elliptically shaped cross section 135 with a plurality of grooves 136 and 137 formed on the outer and inner arcuate surfaces of the needle, respectively. This elliptical cross sectional shape allows the cooperating channel surfaces 116 and 117 and inclined straight contact segment 119 of beveled edge 110 to position the needle in the perpendicular or 90 degree orientation with respect to the longitudinal axis of the instrument. The inclined segment of the beveled edge also facilitates a wide range of cross-sectional dimensions for various sized, commercially available curved suture needles.

Figure 4:
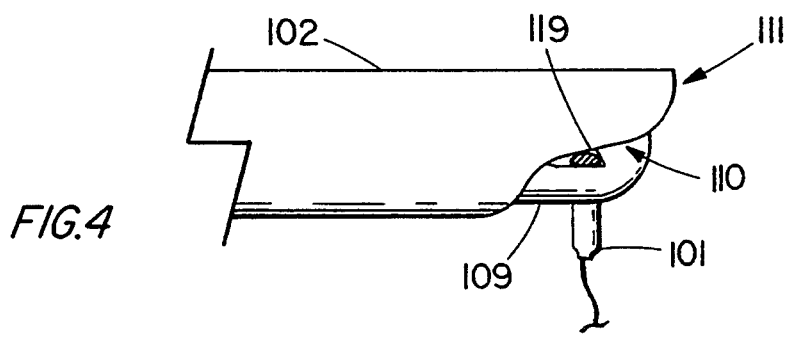
FIG. 4 depicts a partial side view of the needle driver medical instrument of FIG. 3 with the curved suture needle fixedly positioned transversely between the inner and outer elongated members.

FIG. 4 depicts a partial side view of distal end 111 of another embodiment of the medical instrument of FIG. 3 with curved suture needle 101 and beveled edge 110 of outer tube 102 positioned in a downward, rather than an upward, orientation with respect to the handle of the instrument. As depicted, needle 101 is again fixedly positioned between inclined contact segment 119 of beveled edge 110 and the cooperating channel surfaces of inner elongated member rod 109. Curved suture needle 101 is fixedly positioned at an approximately 90 degree orientation with respect to the longitudinal axis of the medical instrument, as shown. As previously indicated, the angles of the channel and contact segments have been experimentally found to hold the suture needle with the greatest amount of force in the preferred, approximately 90 degree orientation with respect to the outer and inner elongated members. This orientation is preferred by surgeons performing operative laparoscopic procedures to enable them to form uniform sutures.

FIG. 5 depicts a bottom view of the medical instrument of FIG. 3 with notch 121 formed in distal end 111 of outer elongated member tube 102 for pushing a suture knot into position during, for example, a minimally invasive surgical procedure. When the medical instrument is not grasping a suture needle, distal end 113 of the inner elongated member rod is withdrawn into the passage of the outer elongated member tube, leaving notch 121 basically unobstructed. The unobstructed notch is used for pushing a knot in suture thread to a desired position in a well-known manner.

As depicted in FIGS. 1-5, outer elongated member tube 102 comprises, for example, a 12.340" long piece of 6.5 gauge thick wall, stainless steel cannula with an outside diameter in a range of 0.187" to 0.189" and an inside diameter in a range of 0.147" to 0.153" for insertion through a commercially available trocar sheath having an inside diameter of commonly 3-10 mm. Beveled edge 110 has contact segments 118, 119, and 120 cut about the circumference of the outer elongated member tube wall. Leading contact segment 118 is positioned at the extreme distal end of the tube and has a 0.080" radius extending axially approximately 0.047" and transversely for approximately 0.0907" or approximately to the centerline of the tube. Trailing contact segment 120 has a 0.090" radius extending axially for approximately 0.082" and terminating at the outside surface of the tube 0.250" back from the extreme distal end of the tube. Intermediate inclined and essentially straight segment 119 extends between leading and trailing contact segments 118 and 120 and has a 0.050" radius at its proximal end that tangentially contacts trailing contact segment 120. Knot pusher notch 121 is formed in leading curved contact segment 118 along the centerline of the tube by cutting back 0.055" from the extreme distal end of the tube and forming 0.930" radius curves 142 and 143 on either side of the notch.

Outer elongated member tube 102 extends from the instrument handle/for a length of approximately 30.5 cm and is preferably positioned back from the extreme distal end of the outer elongated member tube a maximum of 1 mm when the rod is in a fully retracted position. Inner elongated member rod 109 comprises, for example, a 14.4633" long piece of stainless steel rod with a 0.140" outside diameter. Distal end 113 of the inner elongated member rod has a 0.070" radius for presenting an atraumatic hemispherical surface to tissue during extension of the rod from the passage of the outer elongated member tube. Undercut channel surface 116 is formed by cutting into the inner elongated member rod to a depth of 0.100" at an angle of 62° with respect to the longitudinal axis thereof beginning at a point 0.100" proximal to the extreme distal end of the rod. Tapered channel surface 115 is cut beginning at a point 0.450" back from the extreme distal end of the rod at an angle of 13°. Entermediate channel surface 117 is cut parallel to the longitudinal axis of the rod between channel surfaces 115 and 116 for a length of 0.050".

FIG. 6 depicts a partially sectioned and enlarged side view of handle 107 of the instrument of FIG. 1. The handle includes handle tube 123 formed of, for example, a 3.250" long stainless steel tube with a 0.500" outside diameter and a 0.375" inside diameter. The handle tube has a 0.125" diameter hole, the centerline of which is drilled 2.503" from the distal end thereof. The distal end of the handle tube includes a 0.250" length of internal 7/16-20 threads, and the proximal end includes a 0.375" length of internal 7/16-20 threads. Longitudinal slot 124 approximately 1.000" long is cut to a width of 0.187" on the centerline of the handle tube beginning at a point 0.400" from the distal end thereof to pass the distal end of spring 108 therethrough.

U-shaped spring 108 extends laterally and, in particular, perpendicularly from the outside surface of the handle tube for a length of 3.300". The parallel portions of the U-shaped spring are spaced approximately 6 cm apart. Disk-shaped end cap 125, with a center hole for permitting the outer and inner elongated members 102 and 109 to pass therethrough, is threadably attached to the distal end of handle tube 123. Proximal end 134 of outer elongated member tube 102 is positioned 0.200" into a 0.190" diameter counterbored longitudinal bore 139 and soldered therein to the distal end of piston 138 using silver solder. The piston is 1.500" long with a 0.355" outside diameter and has a 0.166" diameter longitudinal bore 139 extending therethrough to pass the proximal end of inner rod 109. The piston also has a 0.166" diameter side port 140 positioned 0.500" from the distal end thereof for passing distal elbow end 128 of the spring into the longitudinal bore and flat recessed section 133 of the inner rod. Rounded, stainless steel end cap 127 is threadably attached to the proximal end of the handle tube for maintaining proximal, loop-shaped end 126 of the spring on the instrument handle. Distal elbow end 128 of the U-shaped spring extends through slot 124 of the handle tube. Cylindrical, plastic material centering sleeve 129 is positioned around the engaging portion of the U-shaped spring positioned through tube handle slot 124. Silicone material tube 130 is positioned over the metal, U-shaped spring flush with both the handle tube and the centering sleeve. Unlike many other surgical instruments, the instrument handle is easily disassembled for a thorough cleaning and sterilization.

Proximal end 122 of inner elongated member rod 109 is attached to a 0.5516" long piece of stainless steel rod 131 with a 0.2500" outside diameter and silver soldered into a 0.1440" end hole 0.200" deep. Rod 131 includes a transverse, 0.1250" diameter hole positioned 0.3915" back from the distal end thereof. Rod 131 is attached to the handle tube using a 0.125" diameter pin 132 positioned transversely through the hole and soldered using silver solder. Flat recessed section 133 is cut to a depth of 0.070" in the inner elongated member rod from a point 1.305" from the extreme proximal end thereof to a point 2.060" therefrom. Distal elbow end 128 of the U-shaped spring moves back and forth in flat recessed section 133 for operating the outer elongated member tube longitudinally with respect to the inner rod.

It is to be understood that the above-described medical instrument for driving a curved suture needle is merely an illustrative embodiment of the principles of this invention and that other apparatus may be devised by those skilled in the art without departing from the spirit and scope of this invention. In particular, the length and outside diameter of the elongated member may be varied to facilitate use in different sized trocar sheaths. This needle driver has been described for use with a curved suture needle. However, the needle driver is also applicable for use with a straight suture needle having a proportionate cross-sectional diameter.

It is also contemplated that the orientation of the captured needle with respect to the longitudinal axis of the instrument can be altered to any desired orientation via the angles of the transverse channel through the inner rod and the contact segments of the outer tube beveled edge. The needle can also be engaged with an upward or downward motion as previously described.

It is further contemplated that other handle configurations can be used in combination with the inner and outer elongated members.

What is claimed is:

1. A medical instrument (100) for driving a suture needle through tissue, comprising:
   an outer, elongated member (102) having a distal end (111), a longitudinal passage (112) therein, and a beveled edge (110) positioned transversely at said distal end thereof; and
   an inner, elongated member (109) positioned in said passage of said outer member, extendable from said distal end of said outer member, and including a longitudinal axis, a channel (114) positioned transversely in said inner member near a distal end (113) thereof and capable of positioning a curved suture needle therein, said beveled edge adapted to fixedly position a curved suture needle in said channel in a predetermined orientation with respect to said longitudinal axis of said inner member when said curved suture needle is positioned in said channel and said beveled edge and said channel are urged toward each other.

2. The medical instrument of claim 1 wherein said channel includes a plurality of channel surfaces (115-117).

3. The medical instrument of claim 2 wherein said plurality of channel surfaces includes an undercut surface (116) forming a first angle in a range of 50 degrees to 90 degrees with respect to said longitudinal axis of said inner member.

4. The medical instrument of claim 3 wherein said plurality of channel surfaces further includes an intermediate surface (117) extending longitudinally from said undercut surface and being substantially parallel to said longitudinal axis of said inner member.

5. The medical instrument of claim 4 wherein said plurality of channel surfaces still further includes a tapered surface (115) extending from said intermediate surface and forming a second angle with respect to said longitudinal axis of said inner member.

6. The medical instrument of claim 5 wherein said second angle of said tapered surface is less than said first angle of said undercut surface for guiding a curved suture needle into said channel of said inner member.

7. The medical instrument of claim 1 wherein said outer member includes a longitudinal axis and wherein said beveled edge includes a substantially straight contact segment (119) inclined at a predetermined angle in a range of 8 degrees to 20 degrees with respect to said longitudinal axis of said outer member for fixedly positioning a curved suture needle in said channel of said inner member in said predetermined orientation.

8. The medical instrument of claim 7 wherein said beveled edge further includes a leading, contact segment (118) for initially engaging and guiding a curved suture needle into said channel.

9. The medical instrument of claim 1 further comprising resilient means (108) for urging said beveled edge and said channel toward each other.

10. The medical instrument of claim 1 further comprising a notch (121) extending longitudinally from said distal end of said outer elongated member.

11. The medical instrument of claim 1 further comprising a handle (107) attached proximate a proximal end of said inner and said outer elongated members.

12. The medical instrument of claim 11 wherein said handle includes a spring (108) having a first end attached proximate said proximal end (122) of said inner elongated member and a second end attached proximate said proximal end (134) of said outer elongated member, said spring urging said beveled edge of said outer member and said channel of said inner member toward each other when a curved suture needle is positioned in said channel.

13. The medical instrument of claim 12 wherein said handle further includes a handle tube (123) and said spring includes a U-shaped portion extending laterally from said handle tube.

14. A medical instrument (100) for driving a curved suture needle through tissue, comprising:
   an outer, elongated member tube (102) having a distal end (111), a longitudinal passage (112) therein, and a beveled edge (110) positioned transversely at said distal end thereof;
   an inner, elongated member rod positioned in said passage of said outer tube, extendable from said distal end of said outer tube, and including a longitudinal axis, a channel (114) positioned transversely in said inner rod near a distal end (113) thereof and capable of positioning a curved suture needle therein, said beveled edge adapted to fixedly position a curved suture needle in said channel in a predetermined orientation with respect to said longitudinal axis of said inner rod when said curved suture needle is positioned in said channel and said beveled edge and said channel are urged toward each other; and
   resilient means (108) attached to said outer tube and said inner member for urging said beveled edge of said outer tube and said channel of said inner rod toward each other.

15. The medical instrument of claim 14 wherein said channel has a plurality of channel surfaces (115-117) including an undercut surface (116) forming a first angle with respect to said longitudinal axis of said inner rod.

16. The medical instrument of claim 15 wherein said plurality of channel surfaces also includes an intermediate surface (117) extending longitudinally from said undercut surface and being substantially parallel to said longitudinal axis of said inner rod.

17. The medical instrument of claim 16 wherein said outer tube includes a longitudinal axis and wherein said beveled edge includes a substantially straight contact segment (119) inclined at a predetermined angle with respect to said longitudinal axis of said outer tube for fixedly positioning a curved suture needle in said channel in said predetermined orientation in combination with said undercut and intermediate surfaces.

18. The medical instrument of claim 17 wherein said beveled edge further includes a leading curved contact segment (118) for initially engaging and guiding a curved suture needle into said channel of said inner rod.

19. The medical instrument of claim 14 further comprising a handle (107) attached proximate a proximal end of said inner rod and said outer tube and including said resilient means and wherein said resilient means includes a spring having a first end attached proximate said proximal end (122) of said inner rod and a second end attached proximate said proximal end (134) of said outer tube, said spring urging said beveled edge of said outer tube and said channel of said inner rod toward each other when a curved suture needle is positioned in said channel.

20. A curved needle driver (100) comprising:
   an outer, elongated member tube (102) having a distal end (111), a longitudinal passage (112) therein, a longitudinal axis and a beveled edge (110) positioned transversely at said distal end thereof, said beveled edge including a leading, curved contact segment (118); an intermediate, substantially straight contact segment (117) inclined at an angle of approximately 12 degrees with respect to said longitudinal axis; and a trailing, curved contact segment (120);
   an inner, elongated member rod (102) positioned in said passage of said outer tube, extendable from said distal end of said outer tube and including a longitudinal axis, a channel (114) positioned transversely in said inner rod near a distal end (111) thereof, and capable of positioning a curved suture needle therein in an approximately 90 degree orientation, said channel including an undercut surface (116) forming an angle of approximately 62 degrees with respect to said longitudinal axis of said inner rod; a tapered surface (115) forming an angle of approximately 13 degrees with respect to said longitudinal axis of said inner rod; and an intermediate surface (117) extending longitudinally between said tapered surface and said undercut surface and being substantially parallel to said longitudinal axis of said inner rod; and
   a handle (107) including a handle tube (123) and a U-shaped spring (108) extending laterally from said handle tube and including a first end attached proximate said proximal end (122) of said inner rod and a second end attached proximate said proximal end (134) of said outer tube, said spring urging said beveled edge of said outer tube and said channel of said inner rod toward each other for positioning said curved suture needle therein in said 90 degree orientation between said substantially straight segment of said beveled edge, said undercut surface, and said intermediate contact surface.

* * * * *